United States Patent [19]

Barrows et al.

[11] Patent Number: 5,502,092
[45] Date of Patent: Mar. 26, 1996

[54] BIOCOMPATIBLE POROUS MATRIX OF BIOABSORBABLE MATERIAL

[75] Inventors: Thomas H. Barrows, Cottage Grove; Myhanh T. Truong, Blaine; Paul R. Suszko, Cottage Grove, all of Minn.

[73] Assignee: Minnesota Mining and Manufacturing Company, St. Paul, Minn.

[21] Appl. No.: 198,906

[22] Filed: Feb. 18, 1994

[51] Int. Cl.⁶ .................................................. C08J 9/28
[52] U.S. Cl. ........................... 521/64; 521/61; 424/486; 424/484; 424/422; 424/423; 424/425; 264/41; 604/890.1
[58] Field of Search ................ 521/64, 61; 424/486, 424/484, 422, 423, 425; 264/41; 604/890.1

[56] References Cited

U.S. PATENT DOCUMENTS

| | | | |
|---|---|---|---|
| 3,902,497 | 9/1975 | Casey | 128/296 |
| 3,937,223 | 2/1976 | Roth | 128/325 |
| 4,186,448 | 2/1980 | Brekke | 3/1.9 |
| 4,343,931 | 8/1982 | Barrows | 528/291 |
| 4,529,792 | 7/1985 | Barrows | 528/291 |
| 4,534,349 | 8/1985 | Barrows | 128/334 R |
| 4,568,536 | 2/1986 | Kronenthal et al. | 424/22 |
| 4,637,931 | 1/1987 | Schmitz | 424/78 |
| 4,669,474 | 6/1987 | Barrows | 128/334 C |
| 4,702,917 | 10/1987 | Schindler | 424/422 |
| 4,719,917 | 1/1988 | Barrows et al. | 128/334 R |
| 4,883,618 | 11/1989 | Barrows | 264/49 |
| 4,892,736 | 1/1990 | Goodson | 424/435 |
| 4,938,763 | 7/1990 | Dunn et al. | 604/891.1 |
| 5,013,315 | 5/1991 | Barrows | 606/71 |
| 5,077,049 | 12/1991 | Dunn et al. | 424/426 |
| 5,286,837 | 2/1994 | Barrows et al. | 528/291 |

FOREIGN PATENT DOCUMENTS

| | | |
|---|---|---|
| 0241178 | 10/1987 | European Pat. Off. . |
| 0244118 | 11/1987 | European Pat. Off. . |
| 0334046 | 9/1989 | European Pat. Off. . |
| 0533262A1 | 3/1993 | European Pat. Off. . |
| 89104635 | 4/1989 | Japan . |
| 2215209 | 9/1989 | United Kingdom . |
| WO89/00842 | 2/1989 | WIPO . |
| WO91/19757 | 12/1991 | WIPO . |
| WO91/19520 | 12/1991 | WIPO . |

OTHER PUBLICATIONS

R. J. M. Zwiers et al., "General crystallization behaviour of poly(L–lactic acid) PLLA: 2. Eutectic crystallization of PLLA", *Polymer*, vol. 24, pp. 167–174, Feb. 1983.

S. Gogolewski et al., "Resorbable materials of poly(L–lactide) III. Porous materials for medical application," *Colloid & Polymer Science*, v. 261, pp. 477–484, 1983.

*Chemical Abstracts* 105(20): 178501P (JP Patent 86,149, 160).

*Chemical Abstracts* 111(16):135710N (JP Patent 89 104635).

U.S. Application Serial No. 07/927,447, filed Aug. 7, 1992.

*Primary Examiner*—James J. Seidleck
*Assistant Examiner*—Duc Truong
*Attorney, Agent, or Firm*—Gary L. Griswold; Walter N. Kirn; Robert H. Jordan

[57] ABSTRACT

A process for forming biocompatible porous matrices of bioabsorbable materials comprising:

a) providing a bioabsorbable polymer;

b) dissolving the bioabsorbable polymer in a volumetric orientation aid to yield a molten solution;

c) solidifying the molten solution to yield an orientation matrix comprising first and second phases, the first phase being the bioabsorbable polymer and the second phase being the volumetric orientation aid; and d) removing the volumetric orientation aid while the solution is solid; to yield a biocompatible matrix of bioabsorbable polymer. Also matrices formed by the process and devices made with such matrices.

31 Claims, 4 Drawing Sheets

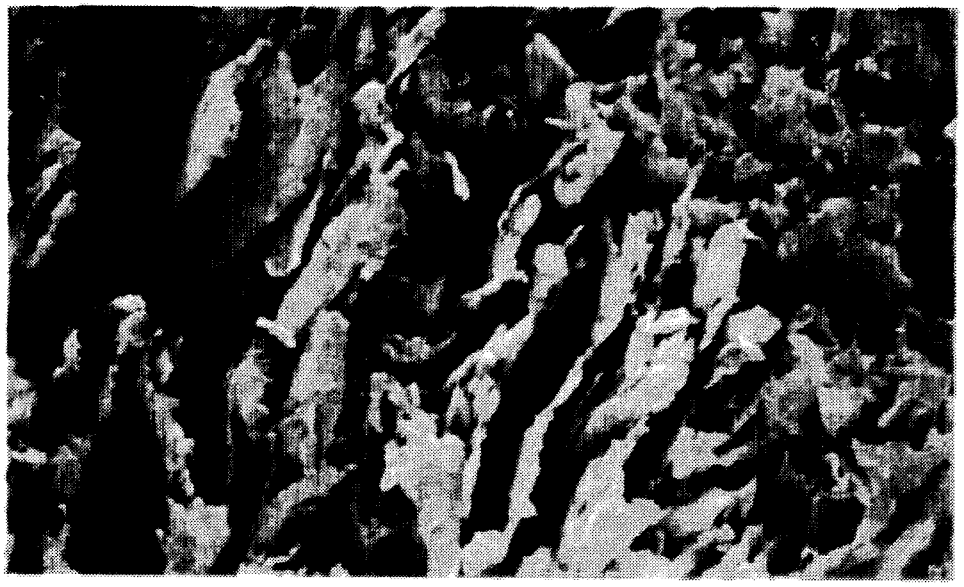
Fig. 1    10 μm
Fig. 2    100 μm

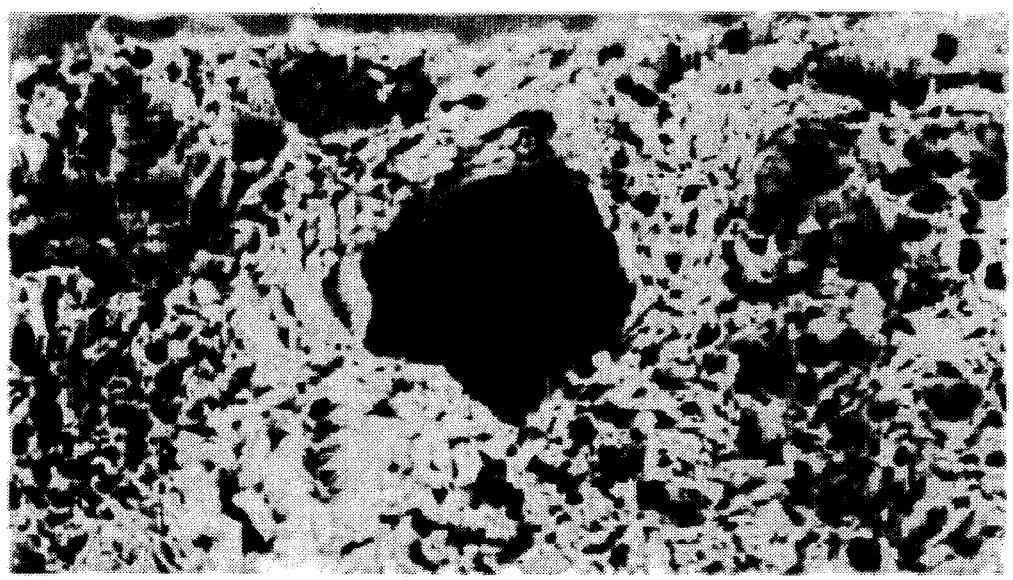
Fig. 3    100 μm
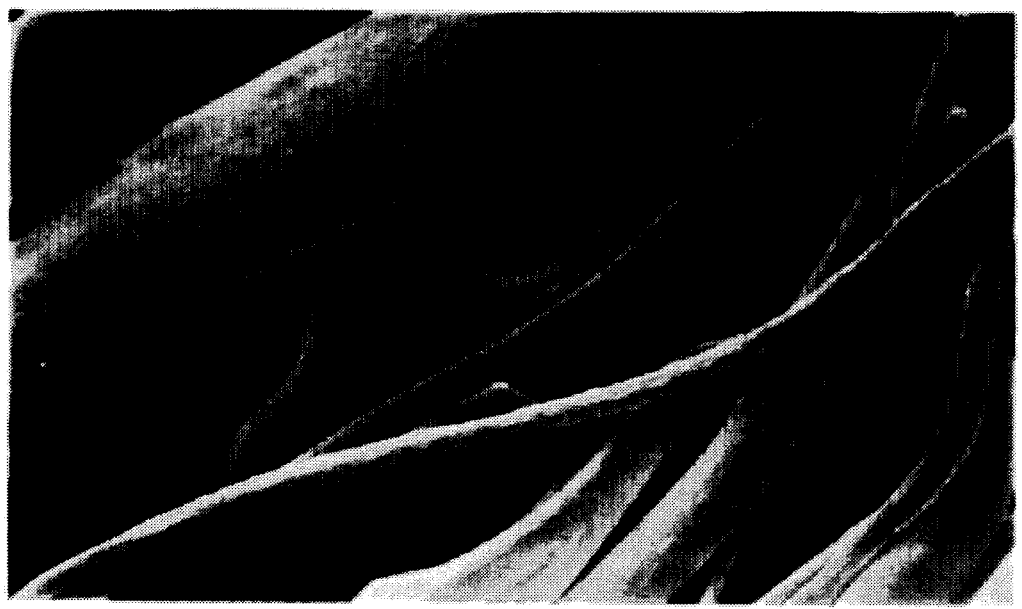
Fig. 4    100 μm

Fig. 5  100 μm
Fig. 6  10 μm

BIOCOMPATIBLE POROUS MATRIX OF BIOABSORBABLE MATERIAL

FIELD OF INVENTION

The present invention relates to bioabsorbable materials and devices made of such materials, and also relates to a method for making such materials and devices.

BACKGROUND

An increasing number of surgically implantable devices that function only for a relatively short period of time in vivo are being designed from synthetic polymers that are eliminated from the body by hydrolytic degradation and subsequent metabolism after serving their intended purpose. Such polymers are commonly referred to as being "bioabsorbable". For example, poly(esteramides) derived from reacting diamidediols with dicarboxylic acids, derivatives thereof, or bischloroformates are known. Such polymers and some of their uses are described in U.S. Pat. Nos. 4,343,931; 4,529,792; 4,534,349; 4,669,474; 4,719,917; 4,883,618; 5,013,315, U.S. Pat. No. 5,286,837; and U.S. application Ser. No. 07/927,447 (all Barrows et al.). Other examples of bioabsorbable polymers include polylactic acid, polyglycolic acid, polydioxanone, poly(lactide-co-glycolide), poly(trimethylene carbonate), polycaprolactone, copolymer of such polymers, or mixture of such polymers.

The use of synthetic bioabsorbable polymers in the design of new surgical devices and drug delivery implants has increased steadily since the first synthetic absorbable suture material made from polyglycolic acid was introduced in the early 1970s. The recent commercialization of polymers and copolymers of lactic and glycolic acids and the reduced regulatory burden involved with developing products made from these materials compared with products made from new synthetic materials has created a demand for novel forms of known polymers and novel fabrication techniques that extend the utility of known bioabsorbable polymers without raising new toxicological safety issues.

A bioabsorbable porous implant for healing a newly created bone void is described in U.S. Pat. No. 4,186,448 which discloses an implant with 90 percent void volume made up of randomly sized, randomly shaped, interconnecting voids. The reference teaches that such voids can be formed via a vacuum foaming process or via a process of forming connected spun filaments containing a wetting agent. The disclosed device is primarily intended for promotion of healing of the cavity or socket resulting from tooth extraction. In spite of its high porosity, the material is essentially incompressible and must be carefully cut to size prior to placement in the socket. Clinical reports of its use confirm the disadvantage of a rigid implant since the slightly oversized implants have caused patients to experience a throbbing pain after anesthesia wears off. Thus there remains a need for a porous bioabsorbable implant that is less rigid and is somewhat compressible and resilient.

Another example of a use for a porous bioabsorbable implant to maintain space and facilitate tissue regeneration is in the case of osteoarthritis of the hand where removal of the trapezium (a wrist bone) is necessary due to pain and limited range of thumb motion. It is known to use silicone rubber spacers as permanent implants, but such implants often become dislocated or lead to complications such as synovitis due to gradual breakdown of the silicone. A more preferred procedure is to fill the void with autogenous connective tissue such as a rolled-up strip of tendon. This permits a more natural healing process in which the transferred tissue can remodel into an effective soft tissue buffer between the remaining bones. A disadvantage of this approach is that it requires an additional surgical procedure to harvest the tendon graft. Another disadvantage of autogenous grafts is the possibility of excessive tissue resorption which produces a clinical result that is substantially equivalent to removal of the bone with no replacement.

Anisotropic compressibility in an implant can be highly desirable. For instance, in the case of a trapezium bone replacement as discussed above, the implant must prevent the metacarpal bone of the wrist from being displaced proximally toward the scaphoid bone of the wrist until adequate density of fibrous tissue can regenerate within the porous structure of the implant. Thus the implant is ideally less compressible in the direction corresponding to axial loading of the metacarpal bone than it is perpendicularly thereto. The biological equivalent of such an anisotropic structure is trabecular bone (also known as cancellous or spongy bone). This type of bone is very low density and provides considerable support in one direction due to the orientation of its mineralized component in such a manner that it possesses maximum strength in relationship to the vectors of the applied loads.

Another application for porous implants relates to recent advances in molecular biology that have created a supply of highly potent growth factors. Thus a porous implant can be treated with minute quantities of growth factors to provide a scaffold that induces the growth of a desired type of tissue thereby resulting in faster regeneration of a reconstructed defect. In cases where the tissue to be regenerated is bone, many different types of materials have been proposed as having an osteogenic or osteoinductive effect. These substances all require the use of a bioabsorbable scaffold or delivery vehicle for clinical utility. For example, U.S. Pat. No. 4,637,931 discloses a technique in which decalcified bone was combined with a solution of a lactide/glycolide copolymer and the solvent evaporated to produce a bone repair material. G.B. Patent Application No. 2,215,209 teaches that bone morphogenetic protein or bone derived growth factor in combination with hyaluronic acid coated on porous polylactic acid provides an effective osteogenic bone graft substitute. The enhanced healing of long bone defects also has been reported with the use of phosphophoryn calcium salt by combining it with an equal amount of collagen and freeze drying the solution to produce a porous sponge. The use of collagen, however, presents a potential risk of an immunological response to the foreign protein.

In addition to vacuum foaming and nonwoven fiber felting processes as cited above, another approach to obtaining a porous structure requires solidification of poly-L-lactide in the presence of additives such as hexamethylbenzene or parahydroxybenzoic acid followed by extraction of the additive. R.J.M. Zwiers, S. Gogolewski, and A.J. Pennings, "General Crystallization Behaviour Of Poly(L-lactic acid) PLLA: 2. Eutectic Crystallization of PLLA", *Polymer,* v. 24, pp. 167-74 (1983). To homogenize the polymer and the additive, prolonged heating at elevated temperature, (i.e., 10° C. above the melting temperature of the highest melting component) is necessary. This temperature requirement limits the utility of this technique to only certain lower melting temperature polymers.

Another method of forming porous articles utilizing crystallization from a solution is disclosed in S. Gogolewski and A.J. Pennings, "Resorbable Materials Of Poly(L-lactide) III Porous Materials For Medical Applications", *Colloid & Polymer Sci.,* v. 261, pp. 477-84, (1983). While these methods were shown to provide control over the pore size obtained, the difficulty in completely removing the additives was acknowledged as a serious practical problem due to their lack of biocompatibility. In many cases a large amount of the additive crystals was discovered to be firmly incorporated into the resultant polymer matrix.

Japanese Patent JP 86,146,160, according to *Chemical Abstracts* 105(20): 178501P, describes a sponge produced from poly-L-lactide or copolymer of lactic acid and other hydroxycarboxylic acids or lactones by dissolving in dioxane, freezing the solution, and freeze drying the resultant solid. A variation on this approach is described in Japanese Patent JP 89,104,635, according to *Chemical Abstracts* 111(16): 135710N, in which sucrose was added to the dioxane solution of polylactic acid prior to freeze-drying. Leaching of the resultant solid yielded a mass with a 97 percent void volume with pores between about 100 and 300 microns.

Dioxane is unique relative to other organic solvents in that it is a good solvent for polylactic acid and its freezing point of 11.8° C. and boiling point of about 100° to 102° C. are close enough to those of water that freeze drying of dioxane solutions can be accomplished in much the same manner as freeze drying of aqueous solutions. Thus freeze drying is not a readily practical method of forming sponges if organic solvents other than dioxane are used. Dioxane, however, presents a severe disadvantage if used to process articles intended for human implantation because of its well-recognized carcinogenic properties. Similarly, the use of hexafluoroisopropyl alcohol or hexafluoroacetone sesquihydrate in the formation of polyglycolic acid sponges and foams as described in U.S. Pat. No. 3,902,497 is undesirable in view of the toxicity of those solvents.

U.S. Pat. No. 4,702,917 discloses a method of forming porous bioabsorbable polyester devices by shaping a blend of the polyester with a polyether followed by selectively eluting the polyether component to form interconnected pores in the remaining polyester mass. The method is reported to yield pores having diameters in the range of 6 to 8 microns. Pores of this size are too small for tissue ingrowth but reportedly were useful in metering high molecular weight drugs through the walls of a tube constructed of such a porous material.

The idea of treating periodontal disease with drug-releasing substances placed under the gum line at the site of infection has been of interest for many years. U.S. Pat. No. 4,568,536 describes a putty-like drug formulation for treatment of periodontal disease in which the matrix comprises a mixture of calcium stearate, dextran, and castor oil. European Patent Application No. 244,118 describes tetracycline loaded polycarbonate microparticles which gave a sustained release of drug for about 25 hours in vitro. This duration was considered adequate since it was estimated that the slow fluid exchange rate of the periodontal pocket would correspond to an in vivo release period of 10 to 20 days. Polycarbonate, however, is not bioabsorbable. Another approach described in European Patent Application No. 241,178 involves the incorporation of tetracycline in a water soluble film made with a copolymer of methacrylic acid and methyl methacrylate. U.S. Pat. No. 4,892,736 discloses a drug-releasing fiber for placement in the periodontal pocket and a retaining means such as an elastic band to keep it in place. Although "glycolic acid polymers" were also claimed, only ethylene vinyl acetate copolymer fibers were shown to produce the desired results. In addition to being too stiff for such an application, polyglycolic acid fibers could not be melt coextruded with tetracycline hydrochloride as taught in this patent without total decomposition of the tetracycline due to the high melting point of polyglycolic acid. U.S. Pat. No. 4,938,763 discloses dissolving poly-L-lactide and sanguinarine hydrochloride (Atrix Labs., Fort Collins, Colo.) in N-methyl pyrrolidinone and injecting this into the periodontal pocket where the polymer and drug coprecipitated in situ to create a bioabsorbable drug delivery implant.

An ideal implant for treating periodontal disease would be a soft, highly compressible material such as a tuft of nonwoven BMF (blown microfibers) that could be inserted into the periodontal pocket without discomfort and without easily becoming dislodged. Such a material ideally would release antibiotic for about a week and then degrade soon thereafter. Polyglycolic acid is an excellent material choice for such an application due to its rapid degradation rate and the fact that it has been used successfully in contaminated surgical sites. The disadvantages of polyglycolic acid in consideration of its use as a drug delivery vehicle, however, result from its high crystallinity, high melting point, and insolubility in all but the most toxic solvents such as hexafluoroisopropanol. Thus while the literature is replete with examples of poly-dl-lactide and lactide-co-glycolide copolymer microspheres and microcapsules for drug delivery, the literature contains no examples of pure polyglycolic acid as a matrix or carrier in the form of BMF fibers for use in drug delivery.

Similar to the periodontal disease treatment implant would be an antibiotic-releasing composition for the treatment of osteomyelitis. In this case the preferred antibiotic is gentamicin. Thin felts of BMF polyglycolic acid also could be treated with broad spectrum antibiotics and used as a prophylactic against wound infection during general closure of surgical incisions.

A BMF form of polyglycolic acid would also be useful as a better topical hemostatic material than that described in U.S. Pat. No. 3,937,223 and as a fast-absorbing reinforcement layer of a bioabsorbable film. European Patent Application No. 334,046 provides further evidence of the potential benefit of such an absorbable material in the surgical treatment of contaminated wounds.

SUMMARY OF INVENTION

The present invention provides novel biocompatible porous matrices of bioabsorbable materials as well as devices made from such matrices and a novel process for making such matrices.

In brief summary, the process of the invention comprises:

a) providing a bioabsorbable polymer;

b) dissolving the bioabsorbable polymer in a volumetric orientation aid to yield a molten solution;

c) solidifying the molten solution to yield an orientation matrix comprising first and second phases, the first phase being the bioabsorbable polymer and the second phase being the volumetric orientation aid; and d) removing the volumetric orientation aid from the solid orientation matrix; to yield a biocompatible matrix of bioabsorbable polymer. Through control of the solidification step, the size and general orientation of the pores can be controlled as desired. In some embodiments, additional agents referred to herein as "voiding agents" are incorporated into the molten solution before it is solidified to form larger openings or pores in the matrix. If desired, the process may also comprise additional steps such as shaping or machining the orientation matrix or biocompatible matrix.

An important advantage of the process of the invention is that it can be performed with biologically well-known materials to yield matrices considered to be biologically safe for implant use, i.e., biocompatible matrices, in addition to being used with other polymers that have not yet been established to be suitable for use as bioabsorbable implants.

Briefly summarizing, the novel matrices of the invention comprise a mass of bioabsorbable polymer having a network of interconnecting pores. The matrix is typically compressible and resilient in some directions. The pores can be oriented in a desired manner so as to impart desired anisotropic compressibility and rigidity to the matrix. Matrices of the invention may be made in resilient form, in a variety of desired shapes, and are chemically very pure. Importantly, when suitable bioabsorbable polymers and orientation aids are used, the resultant matrix is biocompatible. In addition to imparting desired physical strength and compressibility to the matrices, the high void volumes of matrices of the invention reduce the quantity of polymer in the device, thereby reducing the quantity of polymer in the implant that must be absorbed by the body. Also, the high surface to volume ratio of matrices of the invention can provide advantages for desired tissue regeneration.

The novel forms of the bioabsorbable polymers that are provided herein can be used to make a number of useful medical implant devices. The matrices can be made with desired surface to volume ratios, can be made with desired anisotropic compressibility/rigidity characteristics, and can be made in desired shapes. Illustrative examples of the forms that matrices of the invention can be formed into include fibers, rods, tubes, blocks, woven and/or nonwoven webs or fabrics, and a host of machined specialty shapes.

BRIEF DESCRIPTION OF DRAWING

The invention will be further explained with reference to the drawing, wherein:

FIGS. 1–6 are scanning electron microscope images of matrices of the invention after removal of volumetric orientation aid.

Figure 7:
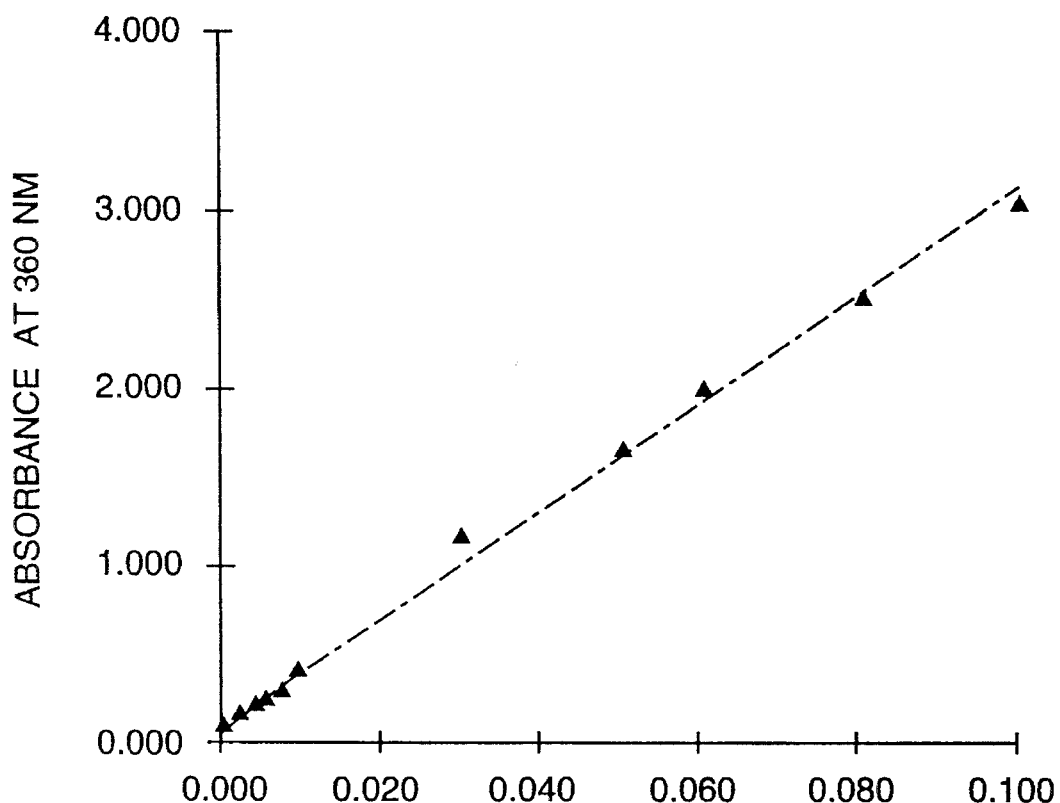
FIG. 7 is a graph of the tetracycline hydrochloride standard plot derived in Example 4 and FIG. 8 is a graph of the tetracycline hydrochloride release results obtained in Example 4.

These figures are intended to be merely illustrative and non-limiting.

DETAILED DESCRIPTION OF ILLUSTRATIVE EMBODIMENTS

As discussed above, the process of the invention comprises:

a) providing a bioabsorbable polymer;

b) dissolving the bioabsorbable polymer in a volumetric orientation aid to yield a molten solution;

c) solidifying the molten solution to yield an orientation matrix comprising first and second phases, the first phase being the bioabsorbable polymer and the second phase being the volumetric orientation aid; and d) removing the volumetric orientation aid while the solution is solid, i.e., from the solid orientation matrix; to yield a biocompatible matrix of bioabsorbable polymer. The polymer is preferably one that is considered or known to be suitable for use in bioabsorbable implants. Thus it is preferably a solid at room and body temperatures. Typically polymers that are substantially solid at 37° C. will be considered suitable. It is preferably considered toxicologically safe for implantation. Illustrative examples of bioabsorbable polymers that can be used in accordance with the invention include the following: polylactic acid, polyglycolic acid, polydioxanone, poly(lactide-co-glycolide), poly-(trimethylene carbonate), polyesteramide, polycaprolactone, copolymer of such polymers, or mixture of such polymers. As used herein, "biocompatible" means the matrix is one that is biologically acceptable both before and after breakdown of the matrix begins. The products produced by breakdown during bioabsorption must be capable of being safely metabolized or excreted by the mammal in which the matrix is implanted.

The volumetric orientation aid is used as described herein to form or shape the mass of bioabsorbable polymer into a desired matrix, i.e., to orient it. Selection of a suitable volumetric orientation aid will depend in part upon the bioabsorbable polymer that is being treated, the desired matrix form, and processing conditions. The volumetric orientation aid should be capable of dissolving the bioabsorbable polymer, preferably substantially without chemically reacting with the polymer, i.e., without substantially changing the molecular weight or chemical composition of the polymer. For instance, the aid should be capable of dissolving the polymer and forming a molten solution at a temperature that is not so high as to degrade the polymer. The aid is preferably considered biocompatible or safe for implant use or convertible into a safe substance upon hydrolysis. In many instances, a volumetric orientation aid that degrades to yield similar biodegradation products as the bioabsorbable polymer itself does can be used. In some of such instances the volumetric orientation aid comprises one or more of a monomer or a dimer precursor of the bioabsorbable polymer. The aid and polymer are preferably such that each one and the mixture are solid at room temperature, i.e., 20° C.

Typically, the volumetric orientation aid is cyclic and has a weight average molecular weight of less than about 1,000 as such materials are more easily processed in the invention.

Illustrative examples of volumetric orientation aids useful in some embodiments of the invention include succinic anhydride, L-lactide, D-lactide, dl-lactide, and glycolide.

After the bioabsorbable polymer and volumetric orientation aid are well mixed to form the molten solution the solution is solidified. It is in the course of this solidification that the orientation and porosity of the resultant matrix are defined. During the course of cooling, the bioabsorbable polymer and volumetric orientation aid separate into two phases. It has been observed that relatively more rapid cooling results in smaller phase domains while relatively slower cooling results in somewhat larger phase domains.

The sizes, distribution, and shapes of the two phase domains and resultant structure of the porous biocompatible matrix depend in part upon the volumetric orientation aid selected and the bioabsorbable polymer being used. For example, matrices formed using succinic anhydride have been observed to exhibit domains having high aspect ratios, i.e., domains that are relatively long and narrow, whereas matrices formed using L-lactide have been observed to exhibit domains that are relatively shorter and more plate-like. It will be understood that mixtures of two or more volumetric orientation aids may be used to achieve combinations of a variety of domains.

The porosity of the resultant biocompatible matrix will depend in large part upon the relative proportions of bioabsorbable polymer and volumetric orientation aid used, with the resultant void volume substantially corresponding to the volume fraction made up of the orientation aid. Typically, the solution will comprise at least about 20 volume percent of volumetric orientation aid, more typically consisting essentially of between about 20 and 97 volume percent of volumetric orientation matrix and 80 to 3 volume percent of the polymer.

An advantage of the invention is that in many instances, solidification of the solution can be achieved by allowing the solution to cool to room temperature. Cooling can be achieved by merely allowing the solution to cool to ambient temperature or by more active means, such as a cooling bath or chamber. An advantage of using such active means is that the rate of cooling can be controlled more precisely to control the phase separation and domain formation process.

The cooling process can be performed in such a manner as to impart a desired shape to the resultant matrix. For example, a rod may be dipped in the molten solution and allowed to cool thereon to form a coating on the rod that can be removed to yield a hollow tube. The solution may be cooled in a mold if desired, e.g., in simple cubic structures or specially selected shapes such as trapezium replacements. After the solution has been solidified, the matrix can be machined, e.g., ground with a lathe, sandpaper, etc. to achieve a desired shape. It is typically preferable to machine the matrix before removal of the volumetric orientation aid as the two phase matrix will be stronger, stiffer, less resilient, and more easily handled than the end product single phase matrix.

Another illustrative useful cooling technique is to spray the molten solution into a fluid stream, e.g., air or an inert gas. Typically the fluid stream will be temperature controlled, e.g., heated, to control solidification of the molten solution. Using this technique, biocompatible matrices of the invention in the form of blown microfibers can be formed.

Depending in part upon the ratio of volumetric orientation aid and polymer, the selection of the aid and polymer, and the conditions of solidification, after solidification the pores in the matrix may not open through the surface of the matrix to as great a degree as would be expected in light of the high porosity of the interior of the matrix.

After the solution is solidified, the volumetric aid is removed. For example, it can be removed by leaching with a solvent, e.g., via continuous extraction. Where the volumetric orientation aid is hydrolyzable with water, e.g., as is succinic anhydride, hydrolysis of the aid with water as an extraction solvent will accelerate the extraction. The solvent is preferably compatible with the bioabsorbable polymer, i.e., will not react with it or degrade it undesirably or dissolve it. Some illustrative examples of suitable combinations include polyglycolic acid polymers that can be treated in accordance with the invention using succinic anhydride as the volumetric orientation aid and acetone as a solvent for leaching and amorphous polylactic acid/polyglycolic acid copolymers that can be treated in accordance with the invention using succinic anhydride as the volumetric orientation aid and water as a solvent for leaching. It will be understood that other combinations of polymer, volumetric orientation aid, and solvent may be used in accordance with the invention.

If desired, the volumetric aid may be removed via sublimation. For instance, during a blown microfiber forming technique as described above, it was observed that a major fraction of the succinic anhydride orientation aid had vaporized, leaving a minor fraction to be leached out with solvent.

Biocompatible matrices of the invention may be made with substantially a single array of pores or with two or more arrays of pores if desired. By "array" of pores, it is meant that the pores will have in common one or more characteristics such as orientation, size, shape, etc. Typically, when solidification of the molten solution is carried out relatively slowly and when a single volumetric orientation aid is used, a single array of pores will result. Two arrays of pores can be achieved by using a suitable second volumetric orientation aid, i.e., one that will tend to form differently shaped domains when the solution solidifies than the domains formed by the first volumetric orientation aid.

Alternatively, a second array of pores can be formed by combining a solid voiding agent in the molten solution before it is solidified. The voiding agent is preferably biocompatible and can be leached out of the matrix with solvent. Preferably the voiding agent does not substantially dissolve in or undesirably react with the bioabsorbable polymer, the volumetric orientation aid(s), or the molten solution thereof. Illustrative examples of suitable voiding agents include particles of one or more of the following: sodium chloride, potassium chloride, calcium chloride, etc. After the molten solution is solidified, the void agent is extracted from the matrix with solvent, e.g., water, passing through the pores in the matrix. The size and shape of the particles will determine the size and shape of the voids or pores formed thereby. The voiding agent may be placed in a mold in desired orientation and arrangement and then the molten solution added to the mold so as to flow around the voiding agent prior to solidifying. The pores formed using a voiding agent can be referred to as a different or second array of pores in the final matrix if they differ in such characteristics as orientation, size, shape, etc.

In one illustrative embodiment, the volumetric orientation aid will yield an array of pores having an average diameter between about 0.5 and about 50 microns and the voiding agent will yield an array of pores having an average size of between about 300 and 500 microns.

Matrices with pores of many desired sizes may be formed in accordance with the invention. Desired pore size will depend in large part upon the intended application of the matrix. For instance, in applications where bone growth or regeneration into the matrix is desired, the matrix will typically have pores greater than about 200 microns. In applications where the matrix is being used as a scaffold or foundation upon which growth of certain cells such as liver, bladder, or cartiledge are desired, the matrix will typically have pores be greater than about 300 microns.

The initial resultant porosity of the biocompatible matrix will be dependent upon the ratio of volumetric orientation aid to biocompatible polymer. For some applications it may be desired to reduce the void volume of the matrix using a secondary treatment. One example is mechanical compression. In another approach, a solvent/plasticizer and compression treatment can be used. In this embodiment, the biocompatible matrix is soaked in a solution comprising, or consisting essentially of, solvent and plasticizer, the solvent being one that will dissolve the plasticizer but only partially dissolve the polymer, and pressure is applied to the matrix. This will result in compression of the matrix with a reduction in void volume. In addition, the solvent action provides some welding of the blades of the polymer in the matrix, thereby imparting greater strength and toughness to the matrix while retaining the general morphology of the structure.

If the biocompatible matrix is merely soaked with a solution comprising, or consisting essentially of, plasticizer and solvent without compression, the solvent being one that dissolves the plasticizer and either does not solubilize or only lowly solubilizes the polymer, the matrix can be plasticized with substantially no change in its void volume. This will impart somewhat greater resiliency to the matrix.

The plasticizers used herein should be biocompatible and capable of plasticizing the polymer. Illustrative examples of plasticizers that can be used in accordance with some embodiments of the invention include glyceryl triacetate and citrate esters (e.g., acetyl tributyl citrate and triethyl citrate).

EXAMPLES

The invention will be further explained by the following illustrative examples which are intended to be non-limiting.

EXAMPLE 1

This example illustrates formation of biocompatible porous matrices of illustrative bioabsorbable polymers (poly-L-lactide ("PLA") having a molecular weight of about 100,000 in Sample 1 and poly(decane-1,10-dicarbonyloxy)methylmethane-1,2-diamidocarbonylethylene ("PEA-10,S2") having an intrinsic viscosity of about 1.10 in Sample 2) in accordance with the invention.

One part by volume of the indicated polymer was dissolved in between three and five parts by volume of molten L-lactide (about 170° C.) as the volumetric orientation aid and the resultant solutions poured into small Petri dishes and allowed to solidify. As each solution cooled, formation of two domains, one of the polymer and one of the L-lactide, was observed in each.

The volumetric orientation aid was removed from each by soaking overnight in a large excess of acetone. After leaching of the volumetric orientation aid, the resultant porous matrices were allowed to air dry.

Analysis of the resultant matrices by scanning electron microscopy ("SEM") revealed a morphology in which the polymer was oriented into substantially uniform blades, separated by spaces ranging from about 5 to about 30 microns wide and oriented in a direction corresponding to the vertical direction when the molten polymer/volumetric orientation aid solution had solidified. FIG. 1 is an SEM photograph at 500× of the resultant PLA matrix sectioned perpendicularly to the direction of volumetric orientation aid solidification revealing the spacing between blades of the PLA. FIG. 2 is an SEM photograph at 50× of the resultant PLA matrix sectioned parallel to the direction of volumetric orientation aid solidification revealing the uniform alignment of the blades of the PLA. Each matrix appeared to be strong and rigid upon manual application of bending and compressive loads. After being soaked for a few minutes in a solution of 10 volume percent triethyl citrate in acetone and then allowing the solution to evaporate, both the poly-L-lactide sample and the PEA-10,2 sample were found to be soft and somewhat resilient. Sample 1 was observed to be somewhat sturdier while sample 2 exhibited a greater tendency to crush when compressed.

EXAMPLE 2

This example illustrates the use of a voiding agent in accordance with the invention.

180 grams of succinic anhydride (Aldrich Chemical Company, cat. no. 13,441-4) were placed in a 250 milliliter three neck round bottom flask and heated in an oil bath at 150° C. under nitrogen with overhead stirring to yield a clear, colorless liquid. Twelve (12) grams of PLA (CCA Biochem, Glorinchem, Holland) were added with continued stirring. The polymer dissolved to yield a clear, colorless, viscous solution.

Reagent grade sodium chloride crystals (Mallinckrodt, Inc.) were sifted through a 28 mesh sieve and collected on a 60 mesh sieve to collect particles between about 250 and about 589 microns in size. 50 grams of this fraction of crystals were added to the molten solution with continuous mixing.

A 3 millimeter (0.125 inch) diameter stainless steel rod was dipped into the mixture and quickly withdrawn. The coating rapidly solidified to yield a hard white solid. An additional 50 grams of the crystal fraction were added and another stainless steel rod similarly dipped and extracted. A third 50 gram portion of the crystals was added and another rod similarly dipped and extracted.

The coated rods were allowed to cool to room temperature and then the coatings sanded to a uniform thickness of about 1.5 millimeters with 100 grit WETORDRY™ Sandpaper (Minnesota Mining and Manufacturing Company). The rods were then soaked overnight in acetone (Mallinckrodt) to leach out the succinic anhydride. The leached rods were then soaked in deionized water for several hours to leach out the sodium chloride crystals. Initially upon placing the rods in the water, concentrated salt solution was observed streaming from the coatings due the schlieric effect. After removal of the salt crystals, the rods were soaked in fresh acetone to remove the water and then allowed to dry in air. The coatings were removed from the rods and the ends trimmed to yield light weight porous tubes having an inside diameter of about 3 millimeters (0.125 inch).

Analysis of the tubes in cross-section by scanning electron microscope ("SEM") revealed that all three tubes were porous matrices having pores of 5 to 50 microns in diameter radiating perpendicularly to the axis of the tube, i.e., parallel to a radius extending from the center of the rod. The inner surface of the tubes, which had been in contact with the rods, was found to have a thin "skin" of PLA having smaller pores. The outer surface, which had been sanded, had no skin and the pores were fully exposed. The tubes had increasing numbers of large voids corresponding to the salt crystal inclusions. FIG. 3 is an SEM photograph at 50× of the exterior surface of a porous PLA tube formed in this Example showing a large pore formed by a sodium chloride crystal and many smaller pores formed by the volumetric orientation aid. The largest voids, about 300 to about 500 microns, were most noticeable and were well separated in the first tube. In the second tube, the large voids were less well separated, i.e., being spaced about 300 to 600 microns apart, and in the third tube the large voids were even more closely spaced, i.e., about 200 to about 500 microns apart. The maximum void volume of the third tube based on the formulation described above and the densities of the ingredients (succinic anhydride has a density of about 15 grams/centimeter$^3$, PLA has a density of about 1.2 grams/centimeter$^3$, and sodium chloride has a density of about 2.2 grams/centimeter$^3$) was calculated to be about 95 percent.

EXAMPLE 3

Using the procedure described in Example 1, biocompatible matrices of the invention were made from the indicated bioabsorbable polymers using, individually, the indicated volumetric orientation aids.

DEXON™ Suture, polyglycolic acid, was found to be processable in accordance with the invention using any of L-lactide (melting point "m.p." of 96° C.), dl-lactide (m.p. 126° C.), glycolide (m.p. 84° C.), succinic anhydride (m.p. 119° C.), and glutaric anhydride (m.p. 55° C.) as volumetric orientation aids. The polymer was not soluble in maleic anhydride (m.p. 52° C.).

PLA was found to be processable in accordance with the invention using any of L-lactide, dl-lactide, glycolide, succinic anhydride, glutaric anhydride, and maleic anhydride as volumetric orientation aids, although the solubility in glycolide was less than in the other aids.

Poly(L-lactide-co-30%-glycolide) was found to be processable in accordance with the invention using any of L-lactide, dl-lactide, glycolide, succinic anhydride, glutaric anhydride, and maleic anhydride as volumetric orientation aids, although the solubility in glycolide was less than in the other aids.

Poly(decane-1,10-dicarbonyloxy)methylene-1,2-diamidocarbonylethylene was found to be processable in accordance with the invention using any of L-lactide, dl-lactide, glycolide, succinic anhydride, glutaric anhydride, and maleic anhydride as volumetric orientation aids, although the solubility in glycolide was less than in the other aids.

PEA-10,S2 was found to be processable in accordance with the invention using any of L-lactide, dl-lactide, glycolide, succinic anhydride, glutaric anhydride, and maleic anhydride as volumetric orientation aids, although the solubility in glycolide was less than in the other aids.

Polydioxanone was found to be processable in accordance with the invention using any of L-lactide, dl-lactide, glycolide, succinic anhydride, glutaric anhydride, and maleic anhydride as volumetric orientation aids.

MAXON™ Suture, glycolide/trimethylene carbonate copolymer, was found to be processable in accordance with the invention using any of L-lactide, dl-lactide, glycolide, succinic anhydride, glutaric anhydride, and maleic anhydride as volumetric orientation aids, although the solubility in L-lactide, dl-lactide, and glycolide was less than in the other aids.

EXAMPLE 4

2 grams of granules of polyglycolic acid were mixed with 8 grams of L-lactide and heated to about 70° C. while stirring, dissolving the polymer in the aid to yield a clear, viscous brown solution.

The molten solution was poured into a stream of nitrogen gas directed toward a tray full of water. The resultant spray solidified on the surface of the water in the form a thin fibrous mat ("orientation matrix"). The mat was carefully skimmed off and placed in a beaker of acetone to dissolve the L-lactide. After a few minutes, the acetone was decanted, fresh acetone added, and the sample allowed to sit overnight. Upon air drying, the fibrous material was white, light weight, and flexible.

Scanning electron microscope analysis showed the fibers to range in diameter greatly, ranging from some as fine as 1 micron in diameter up to some as thick as several tenths of a millimeter. Although the surface of the fibers appeared to be generally smooth, cross-sections of the fibers revealed a microporous interior with submicron-sized pores. FIG. 4 is an SEM photograph at 252× of the blown microfibers produced in this Example. FIG. 5 is an SEM photograph at 250× of blown microfiber produced in this Example wherein the surface or "skin" has been disrupted to reveal the porous interior of the matrix. FIG. 6 is an SEM photograph at 500× of the same disrupted portion shown in FIG. 5.

A 0.380 gram sample of the fibers was placed in an aqueous solution of 10 percent (w/v) tetracycline hydrochloride, Sigma Chemical Company, containing 2 percent (w/v) poly(N-vinyl pyrrolidone), Aldrich Chemical Company, 360,000 molecular weight to suppress crystallization of the tetracycline hydrochloride on the surface of the fiber. The submerged sample was then subjected to a high vacuum for 30 minutes during which time trapped air streamed out of the fibers as a froth of small bubbles. The sample was removed from the liquid, allowed to air dry for a few hours, and then placed under high vacuum for several days to complete drying. The dry sample exhibited a weight gain of 0.567 gram (149 percent) due to absorption of tetracycline hydrochloride.

A 0.380 gram sample of the tetracycline hydrochloride treated fiber was placed in a 20 percent (w/v) solution of MEDISORB™ poly(d,l-lactide-co-50%-glycolide) in chloroform, removed from the liquid, and dried under a gentle flow of nitrogen overnight to form a coated sample. The dry sample exhibited a weight gain of 0.073 grams (19 percent).

Samples of the uncoated and coated tetracycline hydrochloride treated fibers were embedded in SCOTCHCAST™ Electrical Resin No. 8 from Minnesota Mining and Manufacturing Company, and cut into thin cross sections on a Leica LKB Lab Historange Microtome. The sections were mounted in immersion oil and examined under transmitted bright field illumination at magnifications of 100× and 200×. Color photomicrographs clearly showed the presence of yellow tetracycline hydrochloride throughout the interiors of the porous fibers.

The uncoated and coated tetracycline hydrochloride treated fibers were estimated to contain 48 and 40 weight percent tetracycline hydrochloride, respectively. An 8 day in vitro drug release study on each was conducted as described below.

Standardized solutions of 0.1, 0.08, 0.06, 0.05, 0.03, 0.01, 0.008, 0.006, 0.005, 0,003, and 0,001 milligram/milliliter of tetracycline hydrochloride in pH 7.4 phosphate buffered saline solution were prepared. Samples of each standard were separately placed in a cuvette and the absorbance at 360 nanometers for each dilution recorded and plotted to yield a standard plot. The standard plot is shown in FIG. 7.

Figure 8:
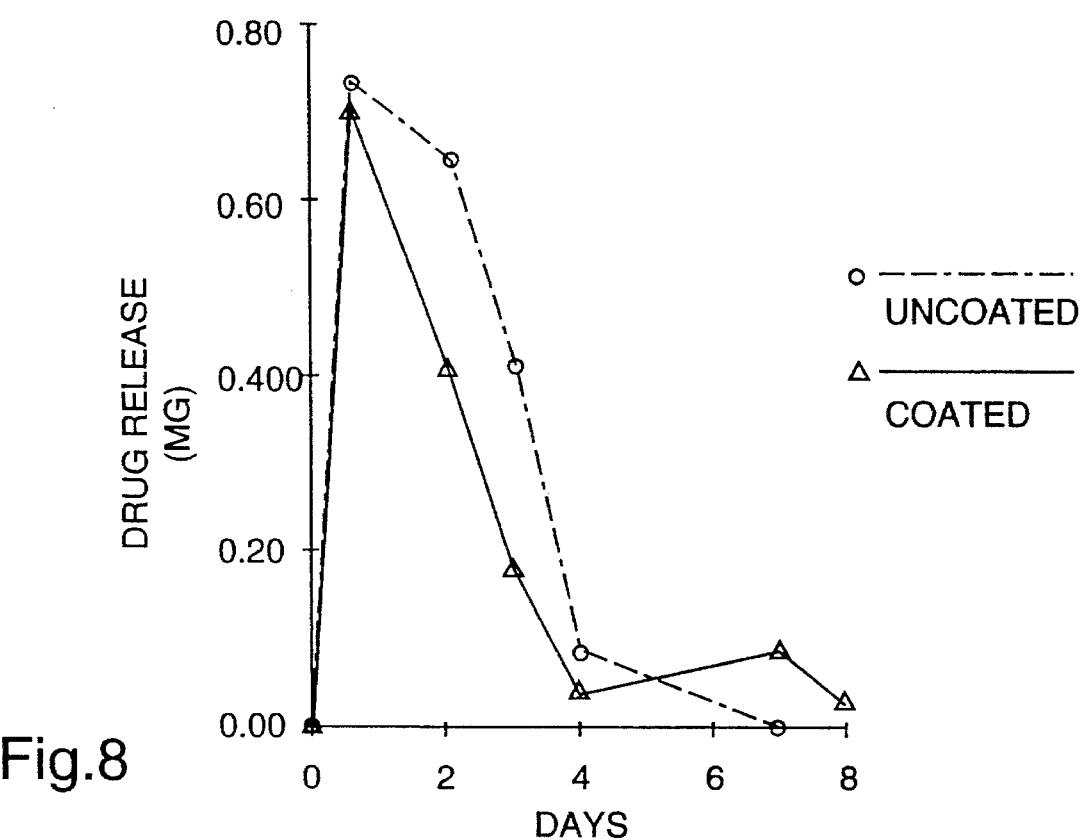

Drug release from both the uncoated and coated fibers was evaluated by placing 50 milligrams of each sample into separate 10 milliliter round bottom flasks, adding 10 milliliters of pH 7.4 phosphate buffered saline solution with a volumetric pipette, and then sealing each flask. The samples were placed in an incubator at 37° C. After 24 hours, the sample solutions were filtered through a Buchner funnel with No. 4 Whatman Filter Paper, and the remaining fibers returned to the flasks which were then refilled with fresh buffered saline solution. This procedure was repeated every 24 hours for 8 days. The absorbance at 360 nanometers of each filtered solution was measures and the drug content of each calculated from the standard plot. The drug release results obtained for each fiber are shown in FIG. 8.

Both uncoated and coated fibers provided prolonged release. A slower, more prolonged release was obtained with the coated sample than with the uncoated sample. Biocompatible matrices of the invention may be coated to provide desired release characteristics.

EXAMPLE 5

75 grams of succinic anhydride (Aldrich Chemical Co.) was melted in a 100 milliliter round bottom flask under nitrogen with mechanical mixing. Three grams of poly(L-lactide-co-30%-glycolide) (Southern Research Institute, inherent viscosity 1.09 deciliters/gram) was added and the mixture heated to 170° C. The polymer dissolved within about 20 minutes to yield a clear solution.

A 3 millimeter diameter, 10 centimeter long, stainless steel rod was placed inside a 5 millimeter inner diameter glass tube and suspended at one end in concentric position by forcing latex rubber splints between the metal and glass. A small piece of glass wool was inserted down the unsuspended end of the rod. The tube was then filled with sodium chloride crystals having a particle size between about 300 and about 500 microns. A rubber hose was attached to the supported end of the tube and connected to a water aspirator to apply a vacuum. The applied vacuum prevented the salt from falling out of the tube when it was inverted. The inverted tube was dipped into the hot polymer solution causing molten solution to flow into the tube up to a height of about 6 centimeters before solidification halted the flow.

After the tube was fully cooled, the glass was gently fractured and removed. The smooth polymer surface was sanded with 100 grit WETORDRY™ Sandpaper (Minnesota Mining and Manufacturing Company) and the coated rod then placed in flowing deionized water for 3 days to fully dissolve and leach out the voiding agent (salt) and volumetric orientation aid (succinic anhydride). The resultant porous tube was gently slipped off the rod, freeze dried, and stored in a desiccator.

The tube had a light weight, fluffy structure with reasonably good physical integrity and flexibility. SEM analysis revealed a highly open structure with interconnected pores of greater than 300 microns formed from the salt crystals and extensive porosity in the range of 5 to 20 microns formed from the succinic anhydride.

EXAMPLE 6

A molten solution of 95 grams of succinic anhydride and 8 grams of poly(L-lactide-co-30%-glycolide) was prepared as in Example 5 and poured into a mold made by centering a 6 millimeter diameter glass rod in a 13 millimeter by 100 millimeter test tube lined with 0.13 millimeter (5 mil) thick TEFLON™ sheeting. After the tube was fully cooled, the outer glass was fractured and removed. The tube was then extracted with water to remove the succinic anhydride and freeze dried. With the inner glass rod still in position, the tube was dipped in an solution of 10 percent (v/v) acetone in cyclohexane containing 6 percent (w/v) of triethyl citrate (Aldrich Chemical Co.). This solution rapidly wicked into the entire volume of the porous matrix. The solution was partially removed by blotting with a rolling action against paper towels and partially removed by evaporation until the thickness of the matrix, initially about 3 millimeters, had decreased to about 1 millimeter. The tube was removed from the glass rod and fully dried under a flow of nitrogen.

The resultant tube, with a reduced void volume, was tough, flexible, and water tight. A control tube made similarly except omitting the triethyl citrate was not as flexible.

Suturability of the plasticized tube was confirmed by placing 5-0 monofilament nylon suture 2 millimeters from the end of the tube and pulling on the suture loop. The suture did not cut through the material when a reasonable level of force was applied. SEM analysis of the tube cross-section before solvent/plasticizer and compression treatment revealed blades of polymer radiating from the inside surface and separated by approximately 5 to 50 microns spacings or pores. SEM analysis after solvent/plasticizer and compression treatment revealed similar blades of polymer arranged in a denser, more random configuration. The outer surface of the tube was relatively smooth, i.e., few pores opening therethrough as compared to the interior of the matrix, because it had not been sanded as in Example 5. The solvent/plasticizer and compression treatment contributed to formation of a water-proof skin on the outer surface of the tube.

Various modifications and alterations of this invention will become apparent to those skilled in the art without departing from the scope and spirit of this invention.

What is claimed is:

1. A process for producing a biocompatible porous matrix of bioabsorbable polymer, said process comprising:
   a) providing a bioabsorbable polymer;
   b) dissolving said bioabsorbable polymer in a volumetric orientation aid to yield a molten solution;
   c) solidifying said molten solution to yield an orientation matrix comprising first and second phases, said first phase being said bioabsorbable polymer and said second phase being said volumetric orientation aid; and
   d) then alter said solidifying removing said volumetric orientation aid from said solid orientation matrix;
   to yield a biocompatible matrix of bioabsorbable polymer.

2. The process of claim 1 wherein said bioabsorbable polymer is a solid at 37° C.

3. The process of claim 1 wherein said bioabsorbable polymer comprises one or more of the following: polylactic acid, polyglycolic acid, polydioxanone, poly(lactide-co-glycolide), poly(trimethylene carbonate), polyesteramide, polycaprolactone, a copolymer of such polymers, or a mixture of such polymers.

4. The process of claim 1 wherein said molten solution comprises at least about 20 volume percent of said volumetric orientation aid.

5. The process of claim 1 wherein said molten solution comprises between about 20 and about 97 volume percent of said volumetric orientation aid and between about 80 and about 3 volume percent of said bioabsorbable polymer.

6. The process of claim 1 wherein said volumetric orientation aid is a solid at 20° C.

7. The process of claim 1 wherein said volumetric orientation aid degrades to yield similar biodegradation products as said bioabsorbable polymer.

8. The process of claim 1 wherein said volumetric orientation aid comprises one or more of a monomer or a dimer precursor of said bioabsorbable polymer.

9. The process of claim 1 wherein said volumetric orientation aid has a weight average molecular weight of less than about 1,000.

10. The process of claim 1 wherein said volumetric orientation aid is succinic anhydride.

11. The process of claim 1 wherein said volumetric orientation aid is L-lactide.

12. A process for producing a biocompatible porous matrix of bioabsorbable polymer, said process comprising:
   a) providing a bioabsorbable polymer;
   b) dissolving said bioabsorbable polymer in a volumetric orientation aid to yield a molten solution;
   c) solidifying said molten solution by reducing the temperature of said molten solution to yield an orientation matrix comprising first and second phases, said first phase being said bioabsorbable polymer and said second phase being said volumetric orientation aid;
   d) shaping said orientation matrix; and then
   e) removing said volumetric orientation aid from said solid orientation matrix to yield a biocompatible matrix of bioabsorbable polymer.

13. The process of claim 12 wherein said solidifying is done by spraying said molten solution into a fluid stream.

14. The process of claim 13 wherein said spraying is done by spraying said molten solution into a heated gas.

15. A process for producing a biocompatible porous matrix of bioabsorbable polymer, said process comprising:
   a) providing a bioabsorbable polymer;
   b) dissolving said bioabsorbable polymer in a volumetric orientation aid to yield a molten solution;
   c) solidifying said molten solution to yield an orientation matrix comprising first and second phases, said first phase being said bioabsorbable polymer and said second phase being said volumetric orientation aid;
   d) shaping said orientation matrix; and then
   e) removing said volumetric orientation aid from said solid orientation matrix to yield a biocompatible matrix of bioabsorbable polymer.

16. A process for producing a biocompatible porous matrix of bioabsorbable polymer, said process comprising:
   a) providing a bioabsorbable polymer;
   b) dissolving said bioabsorbable polymer in a volumetric orientation aid to yield a molten solution;
   c) solidifying said molten solution to yield an orientation matrix comprising first and second phases, said first phase being said bioabsorbable polymer and said second phase being said volumetric orientation aid;
   d) removing said volumetric orientation aid from said solid orientation matrix by leaching with a solvent to yield a biocompatible matrix of bioabsorbable polymer.

17. The process of claim 16 wherein said leaching comprises continuous extraction.

18. The process of claim 16 wherein said solvent is compatible with said bioabsorbable polymer.

19. A process for producing a biocompatible porous matrix of bioabsorbable polymer, said process comprising:
   a) providing a bioabsorbable polymer;
   b) dissolving said bioabsorbable polymer in a volumetric orientation aid to yield a molten solution;
   c) solidifying said molten solution to yield an orientation matrix comprising first and second phases, said first phase being said bioabsorbable polymer and said second phase being said volumetric orientation aid;
   d) removing said volumetric orientation aid from said solid orientation matrix by sublimation.

20. The process of claim 1 further comprising combining a voiding agent with said molten solution before solidifying said molten solution.

21. The process of claim 20 wherein said voiding agent is a solid.

22. The process of claim 20 wherein said voiding agent is substantially insoluble in said molten solution, in said bioabsorbable polymer, and in said volumetric orientation aid.

23. The process of claim 20 wherein said voiding agent is removed from said orientation matrix via leaching.

24. The process of claim 20 wherein said voiding agent comprises particles of one or more of the following: sodium chloride, potassium chloride, or calcium chloride.

25. The process of claim 20 wherein said voiding agent is soluble in water.

26. The process of claim 20 comprising placing said voiding agent in a mold prior to placing said molten solution in said mold.

27. The process of claim 20 wherein said voiding agent comprises particles having an average size of from about 50 to about 1000 microns.

28. A process for producing a biocompatible porous matrix of bioabsorbable polymer, said process comprising:
   a) providing a bioabsorbable polymer;
   b) dissolving said bioabsorbable polymer in a volumetric orientation aid to yield a molten solution;
   c) solidifying said molten solution to yield an orientation matrix comprising first and second phases, said first phase being said bioabsorbable polymer and said second phase being said volumetric orientation aid;
   d) then after said solidifying removing said volumetric orientation aid from said solid orientation matrix to yield a biocompatible matrix of bioabsorbable polymer; and
   e) soaking said biocompatible matrix in a plasticizing solution comprising plasticizer and solvent.

29. The process of claim 28 wherein said plasticizer is one or more of: glyceryl triacetate or a citrate ester.

30. The process of claim 28 wherein said solvent is one or more of: acetone or cyclohexane.

31. The process of claim 28 further comprising compressing said biocompatible matrix while said matrix is soaked with said plasticizing solution.

* * * * *

UNITED STATES PATENT AND TRADEMARK OFFICE
CERTIFICATE OF CORRECTION

PATENT NO.: 5,502,092
DATED: March 26, 1996
INVENTOR(S): Thomas H. Barrows et al.

It is certified that error appears in the above-identified patent and that said Letters Patent is hereby corrected as shown below:

In Column 10, Line 55, the number "15" should read --1.5--.

In Column 12, Line 37, the numbers "0,003" and "0,001" should read --0.003-- and --0.001--, respectively.

Signed and Sealed this

Twenty-seventh Day of August, 1996

Attest:

BRUCE LEHMAN

*Attesting Officer*   *Commissioner of Patents and Trademarks*